United States Patent [19]

Datta et al.

[11] Patent Number: 5,554,239
[45] Date of Patent: Sep. 10, 1996

[54] METHOD OF MANUFACTURING A FASTENING SYSTEM FOR AN ABSORBENT ARTICLE

[75] Inventors: Paul J. Datta, Appleton; Michael A. Machurick, Little Chute, both of Wis.

[73] Assignee: Kimberly-Clark Corporation, Neenah, Wis.

[21] Appl. No.: 435,124

[22] Filed: May 5, 1995

Related U.S. Application Data

[62] Division of Ser. No. 366,077, Dec. 28, 1994, Pat. No. 5,476,702.

[51] Int. Cl.$^6$ .................... A44B 18/00; A61F 13/62; B32B 31/04; B32B 31/12
[52] U.S. Cl. ................... 156/66; 24/442; 24/444; 156/88; 156/265; 156/302; 156/519; 156/547; 156/552; 156/578; 428/99; 604/391
[58] Field of Search ............ 428/99, 100; 604/390, 604/391; 24/DIG. 11, 306, 442, 444, 448, 450, 451; 156/66, 72, 88, 250, 265, 299, 302, 324, 517, 519, 539, 547, 552, 556, 566–569, 578

[56] References Cited

U.S. PATENT DOCUMENTS

| | | |
|---|---|---|
| 3,694,867 | 10/1972 | Stumpf . |
| 4,388,075 | 6/1983 | Mesek et al. . |
| 4,608,115 | 8/1986 | Schroth et al. . |
| 4,662,037 | 5/1987 | Provost et al. . |
| 4,699,823 | 10/1987 | Kellenberger et al. . |
| 4,761,318 | 8/1988 | Ott et al. . |
| 4,776,068 | 10/1988 | Smirlock et al. . |
| 4,904,249 | 2/1990 | Miller et al. . |
| 4,936,840 | 6/1990 | Proxmire . |
| 4,938,754 | 7/1990 | Mesek . |
| 4,973,326 | 11/1990 | Wood et al. . |
| 4,994,054 | 2/1991 | Pigneul et al. . |
| 5,019,073 | 5/1991 | Roessler et al. . |
| 5,032,122 | 7/1991 | Noel et al. . |
| 5,147,343 | 9/1992 | Kellenberger . |
| 5,227,107 | 7/1993 | Dickenson et al. . |
| 5,304,162 | 4/1994 | Kuen . |
| 5,318,555 | 6/1994 | Siebers et al. . |
| 5,374,262 | 12/1994 | Keuhn, Jr. et al. . |
| 5,386,595 | 2/1995 | Kuen et al. . |
| B1 4,315,508 | 11/1988 | Bolick . |

FOREIGN PATENT DOCUMENTS

| | | |
|---|---|---|
| 0319249A1 | 6/1989 | European Pat. Off. . |
| 0341993A1 | 11/1989 | European Pat. Off. . |
| WO95/11655 | 5/1995 | WIPO . |

*Primary Examiner*—Adrienne C. Johnstone
*Attorney, Agent, or Firm*—Thomas M. Gage

[57] ABSTRACT

A fastening component for releasable engagement with a complementary fastener includes a substrate and a first fastener formed of a flexible fabric. An adhesive substance is disposed between and bonded to the first fastener and the substrate. The adhesive substance has a first zone with a first basis weight greater than zero, and a second zone with a second basis weight at least about 1.5 times greater than the first basis weight.

15 Claims, 5 Drawing Sheets

5,554,239

METHOD OF MANUFACTURING A FASTENING SYSTEM FOR AN ABSORBENT ARTICLE

This is a divisional application of application U.S. Ser. No. 08/366,077, filed on Dec. 28, 1994 now U.S. Pat. No. 5,476,702.

BACKGROUND OF THE INVENTION

The present invention relates to articles for absorbing body fluids. More particularly, the invention pertains to a fastening system including a flexible fabric fastener for securing a disposable absorbent article about a wearer.

Disposable absorbent articles such as diapers, incontinence undergarments, feminine products, or the like have heretofore included a wide variety of fastening systems for securing the product about the wearer. For example, previous fastening systems have included tape fastening tabs, garment attachment adhesives, button and button hole systems, snaps, belts, and the like. Previous fastening systems have also included hook-and-loop fasteners which provide several desirable characteristics, such as ease of adjustment for fit, and one-hand application and removal.

Current fastening systems that employ a hook fastener that releasably attaches to a loop fastener have several disadvantages as well. For example, the loop fastener is typically a flexible fabric having a plurality of loops formed on one major surface. The choices for attaching the loop fastener to the underlying substrate may be limited. Adhesives as used heretofore have tended to bleed through the porous fabric of the loop fastener and bond the loops to the base of the loop material. This can significantly reduce the number of loops that are available for attachment to the hook fastener. The alternatives to using adhesives to bond the loop fasteners to the substrate tend to employ additional components or equipment which tend to adversely impact high speed manufacturing techniques.

Therefore, what is lacking and needed in the art is a fastening component that incorporates a fastener made of flexible fabric which is securely held in place without deleteriously affecting performance.

SUMMARY OF THE INVENTION

In response to the discussed deficiencies in the prior art, a new fastening component has been developed. The fastening component provides enhanced resistance to failure resulting from shear forces without necessitating additional components or equipment to bond the fastener to the underlying substrate.

In one aspect, the present invention concerns a fastening component including a substrate and a first fastener formed of a flexible fabric. An adhesive substance is disposed between and bonded to the first fastener and the substrate. The adhesive substance has a first zone with a first basis weight greater than zero, and a second zone with a second basis weight at least about 1.5 times greater than the first basis weight.

In another aspect, the present invention concerns an absorbent article having a first waist region, a second waist region, and a crotch region positioned between and interconnecting the first and second waist regions. The absorbent article includes a moisture barrier, an absorbent assembly disposed on the moisture barrier, and first and second fasteners. The first fastener comprises a flexible fabric, and the second fastener is bonded to the moisture barrier in the second waist region and adapted for releasable engagement with the first fastener. An adhesive substance is disposed between and bonded to the first fastener and the moisture barrier in the first waist region. The adhesive substance includes a first zone with a first basis weight greater than zero, and a second zone with a second basis weight at least about 1.5 times greater than the first basis weight.

In yet another aspect, the invention concerns a method of forming a fastening component. The method includes the steps of: providing a first fastener comprising a flexible fabric; providing a substrate; and applying an adhesive substance between the first fastener and the substrate. The adhesive substance includes a first zone with a first basis weight greater than zero, and a second zone with a second basis weight at least about 1.5 times greater than the first basis weight.

The adhesive substance securely bonds the first fastener to the underlying substrate. The amount of adhesive in the first zone is selected so that the adhesive does not bleed through to the surface of the first fastener that is adapted or engagement to a complementary fastener. The amount of adhesive in the second zone, on the other hand, may be such that it penetrates the first fastener. The second zone provides a region of enhanced bonding between the first fastener and the substrate. The area and position of the second zone are desirably controlled so that the first fastener may thoroughly engage the complementary fastener.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

BRIEF DESCRIPTION ON OF THE DRAWINGS

FIG. 1 representatively shows a perspective view of a disposable absorbent article according to the present invention.

FIG. 2 representatively, shows a plan view of portions of the disposable absorbent article shown in FIG. 1, taken from the outer garment side of the absorbent article in a stretched and laid flat condition and with portions broken away for purposes of illustration.

FIG. 3 representatively shows an enlarged section view taken generally from the plane of the line 3—3 in FIG. 2.

FIG. 4 representatively shows an enlarged section view taken generally from the plane of the line 4—4 in FIG. 2.

FIG. 5 representatively shows an enlarged section view of an exemplary loop material.

FIG. 6 representatively shows an apparatus useful in making fastening components for the absorbent article shown in FIG. 1.

FIG. 7 representatively shows a front view of a shim component of the apparatus shown in FIG. 6.

FIG. 8 representatively shows an enlarged section view similar to FIG. 4 but illustrating an alternative embodiment of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use and not intended to be washed and reused.

(c) "disposed," "disposed on," "disposed with," "disposed at," "disposed near" and variations thereof are intended to mean that one element can be integral with another element, or that one element can be a separate structure bonded to or placed with or placed near another element.

(d) "elastic," "elasticized" and "elasticity" mean that property of a material by virtue of which it tends to recover its original size and shape after removal of a force causing a deformation.

(e) "elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

(f) "extension," "extend" and "extended" mean the change in length of a material due to stretching, expressed in units of length.

(g) "fabrics" is used to refer to all of the woven, knitted and nonwoven fibrous webs.

(h) "flexible" refers to materials which are compliant and which will readily conform to the general shape and contours of the wearer's body.

(i) "force" includes a physical influence exerted by one body on another which produces acceleration of bodies that are free to move and deformation of bodies that are not free to move. Force is expressed in grams per unit area.

(j) "hydrophtlic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(k) "integral" is used to refer to various portions of a single unitary element rather than separate structures bonded to or placed with or placed near one another.

(l) "inward" and "outward" refer to positions relative to the center of an absorbent garment, and particularly transversely and/or longitudinally closer to or away from the longitudinal and transverse center of the absorbent garment.

(m) "layer" when used in the singular can have the dual meaning of a single element or a plurality of elements.

(n) "liquid impermeable" when used to describe a layer or laminate means that liquid such as urine will not pass through the layer or laminate under ordinary use conditions in a direction generally perpendicular to the plane of the layer or laminate at the point of liquid contact.

(o) "member" when used in the singular can have the dual meaning of a single element or a plurality of elements.

(p) "nonwoven web" means a web of material which is formed without the aid of a textile weaving or knitting process.

(q) "operatively joined" and "operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(r) "releasably attached," "releasably bonded," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

(s) "rupture" means the breaking or tearing apart of a material; in tensile testing, the term refers to the total separation of a material into two parts either all at once or in stages, or the development of a hole in some materials.

(t) "stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

(u) "stretch bonded laminate" refers to composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portion of the specification.

DETAILED DESCRIPTION OF THE EMBODIMENTS

Figure 1:
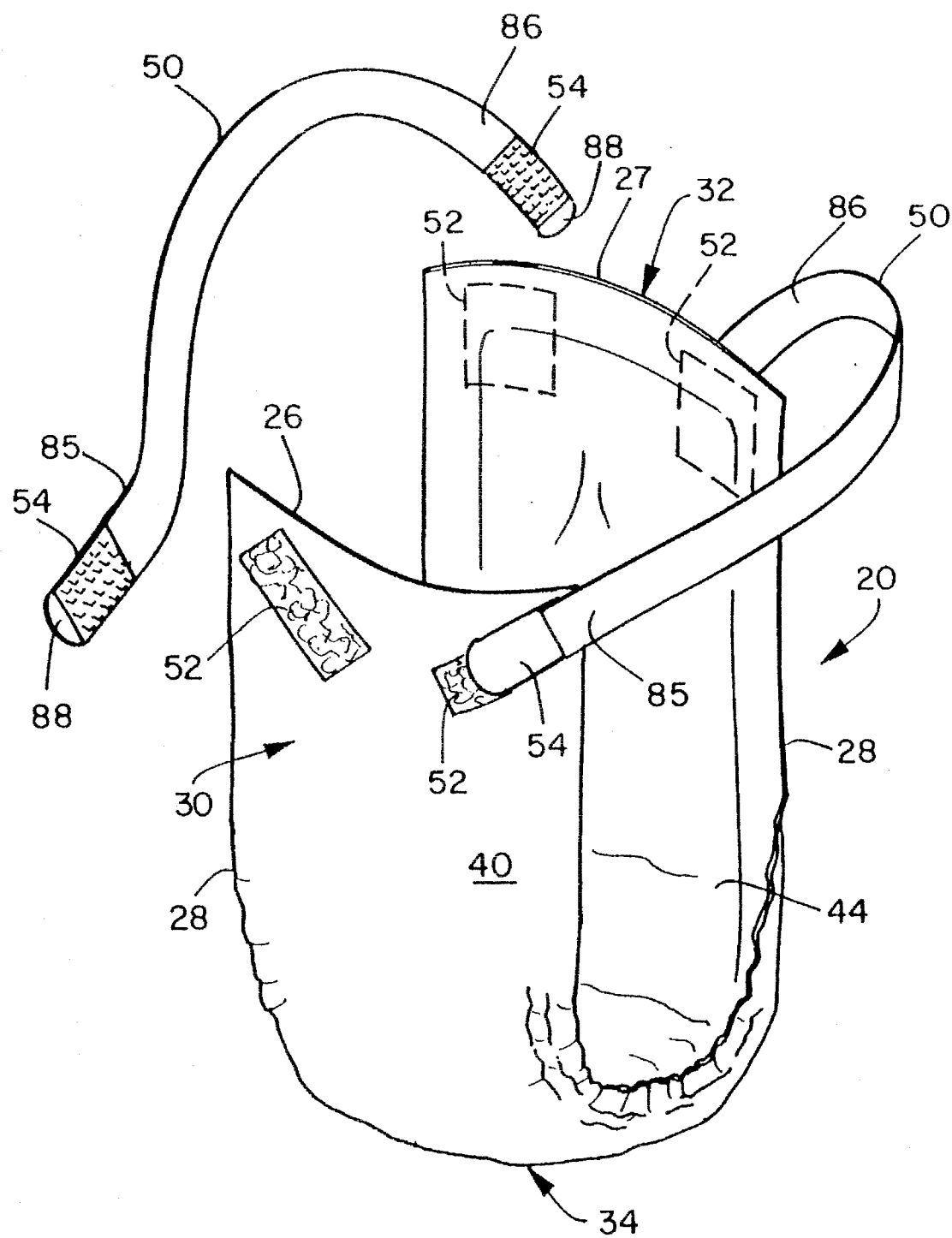

With reference to FIGS. 1–4, an absorbent article formed according to the invention is shown for purposes of illustration as a disposable undergarment 20 for adult incontinence. The invention may also be embodied in other types of garments, such as other disposable absorbent articles, reusable absorbent articles, underwear, bathing suits, athletic supporters, prosthetics, or other personal care or health care garments, or the like.

In general, the undergarment 20 includes first fasteners 52 that are each bonded securely to a substrate 40 by an adhesive substance 80. The adhesive substance 80 has a first zone 81 with a first basis weight greater than zero and a second zone 82 with a second basis weight greater than the first basis weight. The adhesive substance 80 in the first zone 81 assists in bonding the first fastener 52 to the substrate 40 without bleeding through to the engagement surface 62 of the first fastener. The adhesive substance 80 in the second zone 82 may be sufficient to penetrate through to the engagement surface 62 of the first fastener 52, however, the area and positioning of the second zone are controlled so that an ample region of the engagement surface is available to receive a complementary fastener 54.

Figure 2:
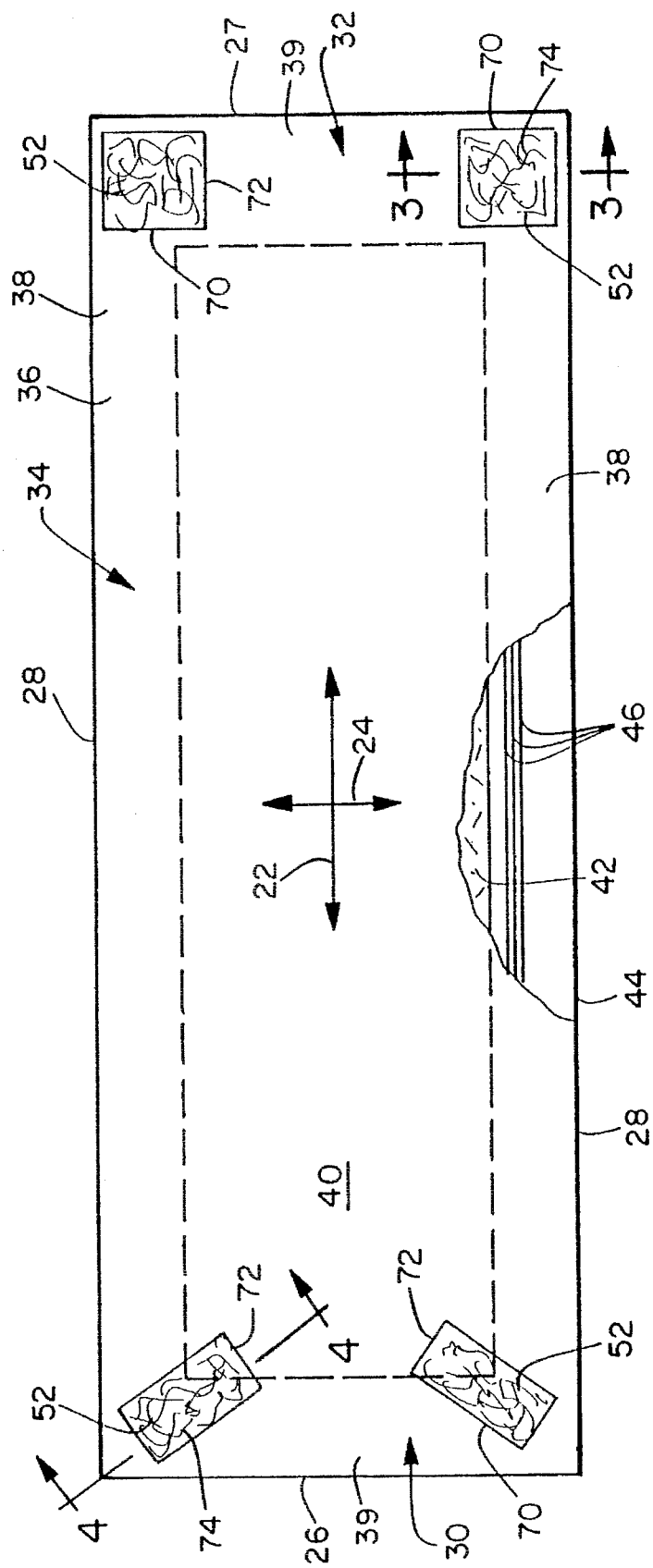

The illustrated undergarment 20 defines longitudinal and transverse axes, represented by arrows 22 and 24 in FIG. 2. The undergarment 20 has opposite, front and back longitudinal end edges 26 and 27, and longitudinal side edges 28 that extend between the longitudinal end edges. The undergarment 20 includes a first or front waist region 30, a second or back waist region 32, and an intermediate, crotch region 34 positioned between and interconnecting the front and back waist regions. The outer edges of the undergarment 20 define a periphery 36 in which the longitudinally extending side margins are designated 38 and the laterally extending end margins are designated 3g. The end edges 26 and 27 and side edges 28 are shown as generally straight, but optionally, may be curvilinear and contoured.

The front waist region 30 is contiguous with the front end edge 26 and extends longitudinally inward therefrom toward the transverse center line of the undergarment 20. The back waist region 32 is contiguous with the back end edge 27 and extends longitudinally inward therefrom toward the transverse center line. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer. Thus, the crotch region 34 is the area where insults of urine typically occur in the undergarment or other disposable absorbent article.

The undergarment 20 includes a substantially liquid impermeable moisture barrier 40, an absorbent assembly 42 (FIG. 2) disposed on the moisture barrier, and a substantially liquid permeable bodyside liner 44 bonded to the moisture barrier to sandwich the absorbent assembly therebetween. The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The peripheries of the moisture barrier 40 and the bodyside liner 44 typically form the side and end margins 38 and 39 of the undergarment 20. The absorbent assembly 42 may be bonded directly to the moisture barrier 40 and/or the bodyside liner 44 using ultrasonic bonds, thermal bonds, adhesives, or other suitable means.

The moisture barrier 40 desirably comprises a material that is formed or treated to be liquid impermeable. Alternatively, the moisture barrier 40 may comprise a liquid permeable material and other suitable means (not shown), such as a liquid impermeable layer associated with the absorbent assembly 42, may be provided to impede liquid movement away from the absorbent assembly. The moisture barrier 40 may also be gas permeable, such that gases encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene medium-crimped bicomponent fibers in a 50/50 side-by-side configuration.

The absorbent assembly 42 comprises materials adapted to absorb and retain liquid waste. The absorbent assembly 42 may comprise various absorbent materials, such as an airformed batt of cellulosic fibers (i.e., wood pulp fluff) or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. Nos. 4,699,823 issued Oct. 13, 1987, to Kellenberger et al. and 5,141,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids (not shown).

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably nonelastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Rohm and Haas Co. under the trade designation Triton X-102.

The undergarment 20, portions of which are in a stretched and laid flat condition in FIG. 2, is illustrated as having a rectangular periphery 36. Of course, the undergarment 20 may optionally be hourglass-shaped, I-shaped, T-shaped, or irregularly-shaped. The general shape of the absorbent assembly 42 may correspond to the shape of the undergarment 20 or assume a different shape.

Desirably although not necessarily, the undergarment 20 also includes leg elastic members 46 to draw and hold the side margins 38 of the undergarment 20 against the legs of the wearer and form a seal therewith. The elongated leg elastic members 46 are longitudinally orientated in each side margin 38, extending toward the front and back end edges 26 and 27. The leg elastic members 46 are positioned in the illustrated embodiment between the moisture barrier 40 and the bodyside liner 44. Using ultrasonic bonds, adhesives, thermal bonds, or other suitable means, the leg elastic members 46 are attached in a stretched condition to the moisture barrier 40, the bodyside liner 44, or both, in either a straight or a curved shape. Alternatively, the leg elastic members 46 may be attached in a relaxed state to a gathered portion of the moisture barrier 40, the bodyside liner 44, or both.

The leg elastic members 46 may be formed of a dry-spun coalesced multifilament elastomeric thread sold under the tradename LYCRA and available from E.I. Du Pont de Nemours and Company. Alternately, the elastic members may be formed of other typical elastics utilized in the undergarment-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. Nos. 4,938,754 to Mesek and 4,388,075 to Mesek et al.

The attachment system in the illustrated embodiment includes a pair of strap members 50 and fastening components to releasably attach the strap members to the front and back waist regions 30 and 32. The fastening components have complementary fasteners 52 and 54 with surfaces that are adapted to repeatedly, releasably engage one another. The fasteners 52 and 54 are adapted to resist disengagement in a shear mode yet easily release from one another in a peel mode. This releasable engagement is accomplished mechanically rather than adhesively. Suitable fasteners include self-engaging geometric shaped materials such as hooks, loops, bulbs, mushrooms, arrowheads, balls on stems, or the like.

The fastening components of the illustrated undergarment 20 include four first fasteners 52 bonded to the moisture barrier 40 and four second fasteners 54 bonded to the strap members 50. In the illustrated embodiment, the first fasteners 52 are formed of a loop material and will also be referred to as loop fasteners 52, and the second fasteners 54 are formed of a hook material and will also be referred to as hook fasteners 54. These fasteners 52 and 54 comprise the complementary components of a hook-and-loop fastening system. It should be appreciated that the location of the hook-and-loop fasteners can be reversed, or that other suitable mechanical fasteners can be substituted for the hook-and-loop fasteners.

Figure 5:
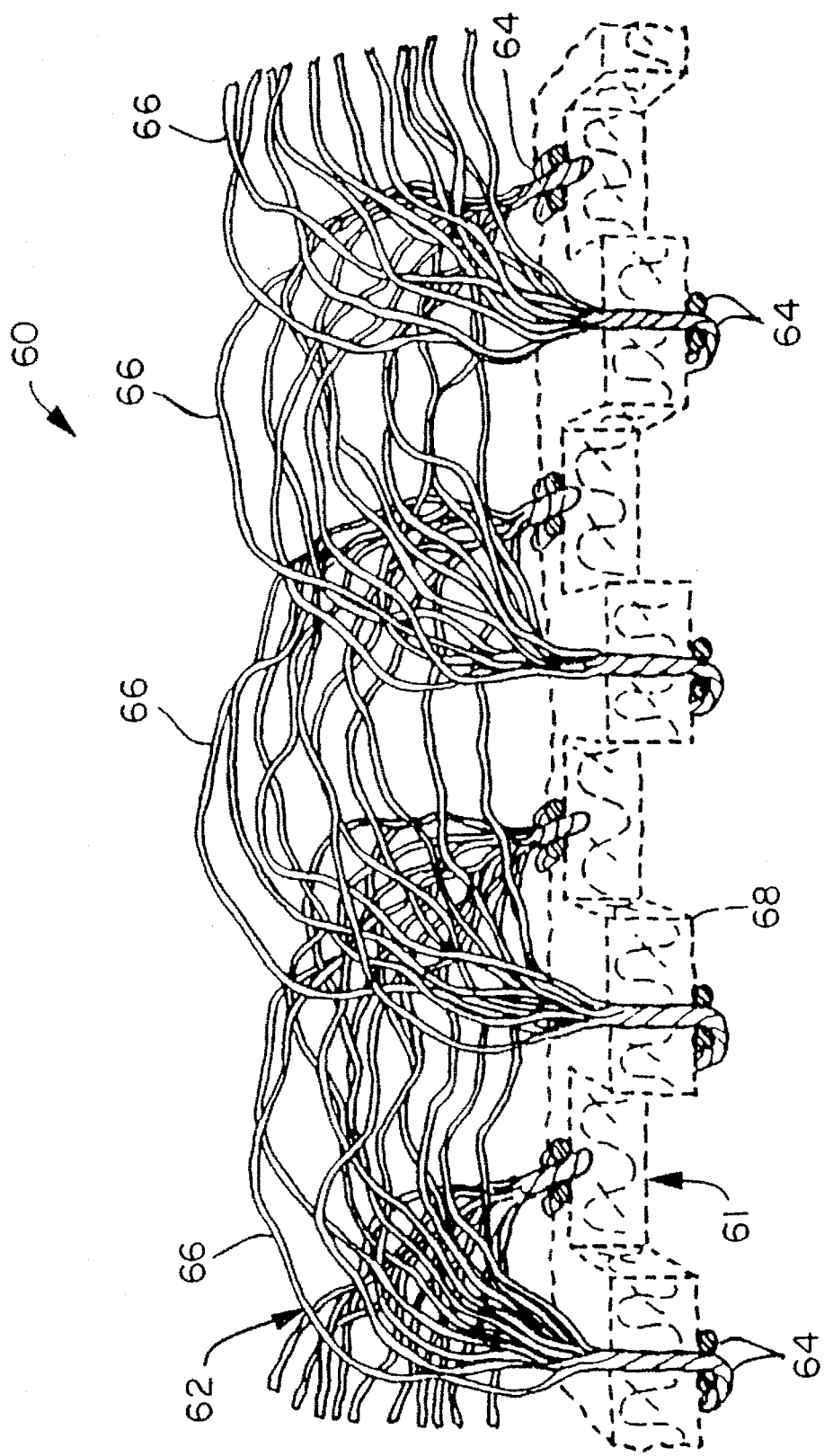

The term loop material is intended to mean any fabric having a base portion and a plurality of loop members extending upwardly from at least one surface of the base portion. An illustrative loop material 60 is representatively shown in FIG. 5. The loop material 60 is a flexible fabric material having opposite major surfaces designated first major surface 61 and second major surface 62. The loop material 60 comprises yarns 64 that are arranged to provide a raised loop construction in which the fabric is stabilized so that loops 66 are erect from the base 68 of the fabric.

The loop material 60 may be formed of any suitable material, such as acrylic, nylon or polyester, and may be formed by methods such as warp knitting, stitch bonding or needle punching. The loop material 60 can be stabilized through napping, thermosetting or the like so that the individual loops 66 are erect from the fabric base 68. The loop fasteners 52 can also be any suitable material having non-woven loops thereon. The loop material 60 may optionally include a sizing (not shown), such as a vinyl acetate copolymer sizing available from National Starch and Chemical Corp. under the trade designation RESYN 5904, applied by mist deposition or other suitable means to the base 68 to a final concentration of less than about 4 weight percent.

In a preferred embodiment, the loop fasteners 52 are formed of a loop material 60 having a two bar warp knit construction, with from 21 to 41 courses per inch (ca. 8–16 per cm.) and from 26 to 46 wales per inch (ca. 10–18 per cm.), of polyester yarn. In particular, about 15-35 percent of the yarns may be composed of yarn having about 1-30 individual filaments therein and having a yarn denier within the range of about 15–30 d (denier). In addition, about 65-85 percent of the yarns may be composed of yarn having about 1-30 individual filaments therein and having a yarn denier within the range of about 20–55 d. Also, the loops may particularly be formed with a loop height from about 2 to about 2.5 millimeters. The loop caliper may be from about 0.010 to about 0.040 inch (ca. 0.25–1 mm.) and the basis weight may be from about 1.0 to about 3.0 ounces per square yard (ca. 34–102 grams per square meter). One particular loop material 60 which has been found suitable for the loop fasteners 52 is identified as No. 19902 and is available from Guilford Mills of Greensboro, N.C.

Figure 3:
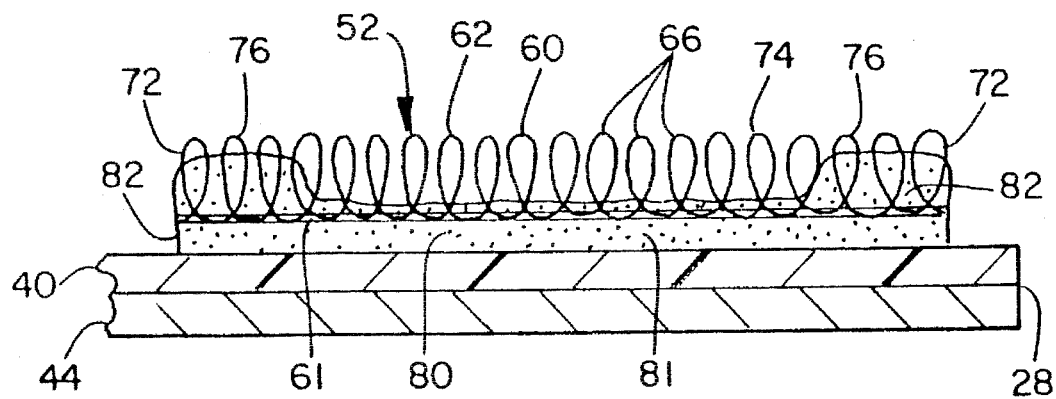
Figure 4:
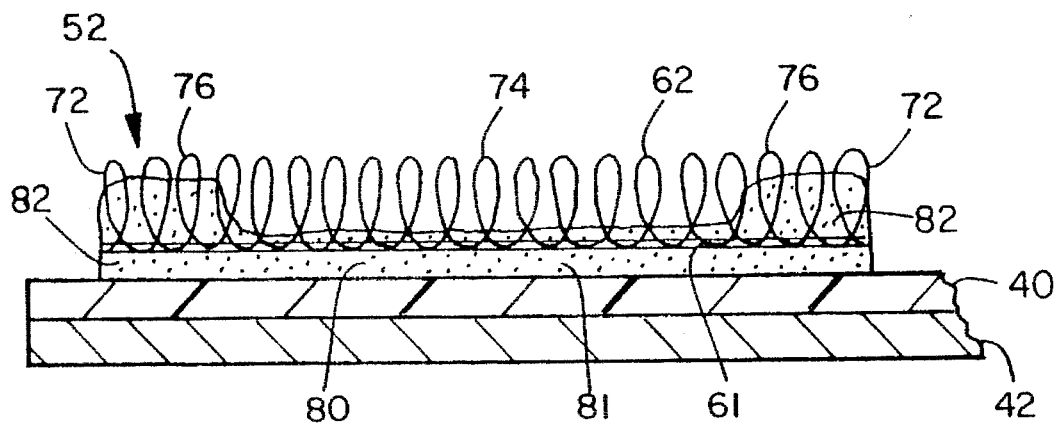

With additional reference to enlarged FIGS. 3 and 4, the loop fasteners 52 are bonded to the surface of the moisture barrier 40 that is remote from the bodyside liner 44. Each of the loop fasteners 52 has opposite side edges 70 and opposite end edges 72. The terms side edges and end edges are most adaptable to rectangular or nearly rectangular loop fasteners 52 where there is a distinct long dimension. Where the loop fasteners 52 are square, oval, curved or otherwise nonrectangularly shaped, the distinction between side edges 70 and end edges 72 becomes somewhat arbitrary and is less significant.

Each of the loop fasteners 52 has a medial region 74 centrally located between the side and end edges 70 and 72. The medial region 74 represents the principal engagement area for the fastener and generally constitutes from about 40 to about 98 percent of the surface area of the loop fastener 52. Each of the loop fasteners 52 also has peripheral portions 76 that are contiguous with the side and edge edges 70 and 72 and extend inward therefrom to the medial region 74. The peripheral portions 76 represent outer areas of the loop fasteners 52 which are, in the present invention, more securely bonded to the underlying substrate than the medial region 74. The peripheral portions 76 generally constitute from about 2 to about 60 percent of the surface area of the loop fastener 52, and particularly less than about 30 percent of the surface area.

The loop fasteners 52 in each waist region 30 and 32 are desirably separated from one another and positioned adjacent the opposite sides edges 28. Desirably although not necessarily, the loop fasteners 52 are also spaced from the front and back end edges 26 and 27 and the side edges 28 by at least about 0.25 inch (ca. 6.5 mm.). Alternatively, there may be a greater number or a lesser number of loop fasteners 52 bonded to the moisture barrier 40 (not shown).

The loop fasteners 52 in the front and back waist regions 30 and 32 may be the same size and be symmetrically positioned. More desirably, however, it has been determined that the particular loop fasteners 52 disclosed herein provide adjustability for the attachment system and at the same time promote the proper orientation of the undergarment 20 on the wearer. In particular, the loop fasteners 52 are desirably attached at specified angles in relation to the longitudinal and transverse axes 22 and 24 of the undergarment 20 in order to promote a proper orientation of the garment on the wearer.

The loop fasteners 52 in the front waist region 30 are desirably rectangular in shape measuring approximately 1.25 inches by 3.38 inches (ca. 3 by 9 cm.). Each loop fastener 52 in the front waist region 30 is bonded to the moisture barrier 40 such that the longitudinal axis of the fastener is directed generally toward the nearest corner of the undergarment 20 and forms an angle in the range of from about 25 to about 45 degrees with the transverse axis 24. The term longitudinal axis in reference to the fastener 52 is used to mean the axis parallel to the longer dimension of the fastener.

Each loop fastener 52 in the back waist region 32 is desirably at least 1 inch by 1 inch (ca. 25 by 25 mm.), providing a surface area of at least about 1 in$^2$ (ca. 6.25 cm$^2$). For example, the loop fasteners 52 in the back waist region 32 may be rectangular and measure 1.5 inch by 2.0 inch (38 by 51 mm.), with the longer dimension of the fastener aligned with the transverse axis 24 of the undergarment 20. Alternately, the loop fasteners 52 in the back waist region 32 could be formed as a single pad of loop material (not shown) attached across the back waist region 32.

The loop tip orientation of the loop fasteners 52 has been found to affect performance of the attachment system. The preferred loop material 60 will have a loop tip orientation (not shown) in a single direction. As used herein, loop tip orientation refers to the general direction in which the tips of the loop members 66 are bent. This direction, which will be in the plane of the loop material, is caused by the napping process used to make the loop material. However, the loop tip orientation may be generated by other processes as well, such as brushing, scraping, nipping, rolling, pressing, differential crepeing, combing and so forth. The loop tip orientation of a loop material can be established by selecting appropriate manufacturing processes and equipment as known in the art.

Desirably, the loop tip orientation of either loop fastener 52 in the front waist region 30 is generally perpendicular to the longitudinal axis of the fastener and directed toward the front end edge 26 of the undergarment 20. Furthermore, the loop tip orientation of either loop fastener 52 in the back waist region 32 is desirably generally parallel to the longitudinal axis 22 of the undergarment 20 and directed toward the opposite or front end edge 26 of the undergarment. Alternately, however, the loop tip orientation of either loop fastener 52 in the back waist region 32 could be generally parallel to the transverse axis 24 of the undergarment 20 and directed toward the other loop fastener 52 in the back waist region. Further arrangements of the loop fasteners are disclosed in U.S. Pat. No. 5,386,595 issued Feb. 1, 1995, to D. Kuen et al. which is incorporated herein by reference.

As representatively illustrated in FIGS. 3 and 4, the loop fasteners 52 are bonded to the moisture barrier substrate 40 with an adhesive substance 80. The adhesive substance 80 is disposed between the first major surface 61 of the loop fastener 52 and the moisture barrier substrate 40 and is effective to bond those surfaces together. The adhesive substance 80 may comprise any suitable adhesive such as a hot melt, or the like. By way of illustration, the adhesive substance 80 may comprise a styrene-isoprene-styrene rubber block copolymer based adhesive containing a rosin ester tackifying resin. One suitable adhesive is available from Findley Adhesives, Inc. of Wauwatosa, Wis., U.S.A., under the trade designation H2122.

The adhesive substance 80 includes a first zone 81 and at least one second zone 82, which represent portions having different basis weights of adhesive. The first and second zones 81 and 82 desirably comprise different regions of an integral mass of adhesive 80. Alternatively, the first and second zones 81 and 82 may comprise separate masses of adhesive 80 that are placed with or placed near one another. The first and second zones 81 and 82 desirably abut one another. As a further alternative, however, there may be a transition zone (not shown) having an intermediate basis weight or a gap (not shown) having no basis weight between the first and second zones 81 and 82. The basis weight of adhesive 80 in either the first zone 81 or the second zone 82 can be determined according to the Basis Weight Test as set forth in the TEST PROCEDURES section below.

The first zone 81 has a basis weight which will be referred to as a first basis weight, and the second zone 82 has a basis weight which will be referred to as a second basis weight. The first basis weight is greater than zero so that the first zone 81 comprises a level of adhesive that functions to bond, albeit relatively lightly, the corresponding portions of the loop fastener 52 and the substrate 40. The particular basis weight of adhesive selected for the first zone 81 will depend upon various factors, such as the type of adhesive, the projected use of the fastener, the type of loop material, the thickness of the fastener, and similar considerations. The first basis weight should be selected so that the adhesive substance 80 does not bleed through from the first zone 81 to the loops 66 of the first fastener 52. The first basis weight may, for purposes of illustration, be from about 0.003 to about 0.01 grams per square centimeter (g/cm$^2$), such as about 0.004 g/cm$^2$.

By comparison, the second basis weight is at least about 1.5 times greater than the first basis weight. More desirably, the second zone 82 has a second basis weight that is at least about 2 times greater, and more particularly from about 4 to about 20 times greater, than the first basis weight for improved performance. While again recognizing that the basis weight of adhesive 80 selected for the second zone 82 will depend upon various factors, it may be stated for purposes of illustration that the adhesive substance 80 in the second zone 82 may have a basis weight of about 0.019 g/cm$^2$.

The increased basis weight of adhesive 80 in the second zone 82 as compared to the first zone 81 functions to more securely bond those portions of the loop fastener 52 and the substrate 40 that correspond to the second zone. In fact, the adhesive 80 in the second zone 82 may even bleed through the base 68 (FIG. 5) of the loop material 60 and effectively deaden some of the loops 66 so they are not effective to engage the hook fasteners 54. The overall performance of the loop fastener 52 is enhanced as a result of the secure attachment afforded by the higher basis weight of the second zone 82. Despite the possible bleed through of adhesive 80 from the second zone 82, performance can be enhanced because the second zone 82 desirably covers much less area than the first zone 81. The surface area covered by the first zone 81 may be as little as about 60 percent of the surface area covered by the second zone 82, but more particularly the surface area of the first zone 81 is greater than the surface area covered by the second zone 82, and desirably is at least about six times greater for improved performance. The larger surface area of the first zone 81 ensures that an adequate number of loops 66 will not be deadened and will be available to releasably secure the hook fastener 54.

To enhance securement of the loop fasteners 52 to the moisture barrier substrate 40 while maintaining adequate shear resistance between the loop and hook fasteners, 52 and 54, the adhesive substance 80 is desirably applied so that the location of the first zone 81 corresponds to the medial region 74 of the loop fastener. Correspondingly, the adhesive substance 80 is applied so that the location of the second zones 82 correspond to the peripheral portions 76 of the loop fastener 52. As a result, even if the loop material 60 is relatively porous and the added amount of adhesive 80 in the second zones 82 bleed through the loop material, only the loops 66 in the peripheral portions 76 of the fastener 52 will be deadened. The lower level of adhesive 80 in the first zone 81 should not bleed through the medial region 74 and thus the loops 66 in the medial region will be available for engagement with the hook fasteners 54.

The second zone 82 may form a continuous zone of relatively high basis weight adhesive that circumscribes the medial portion 74. Alternatively, one or a plurality of second zones 82 may bond a loop fastener 52 to the moisture barrier substrate 40. In the illustrated embodiment, the loop fasteners 52 in the front and back waist region 30 and 32 are bonded to the moisture barrier substrate 40 with two second zones 82 of adhesive 80 that are oriented along the end edges 72 of the loop fasteners 52 (FIGS. 3 and 4). Desirably, the second zones 82 are located within about 3 cm of the side or end edges 70 and 72 of the loop fasteners 52, and more particularly within about 0.5 cm for improved performance. Alternatively, the loop fasteners 52 could be bonded to the moisture barrier substrate 40 with two second zones 82 of adhesive 80 oriented along the sides edges 70 of the loop fasteners 52 (not shown).

Figure 6:
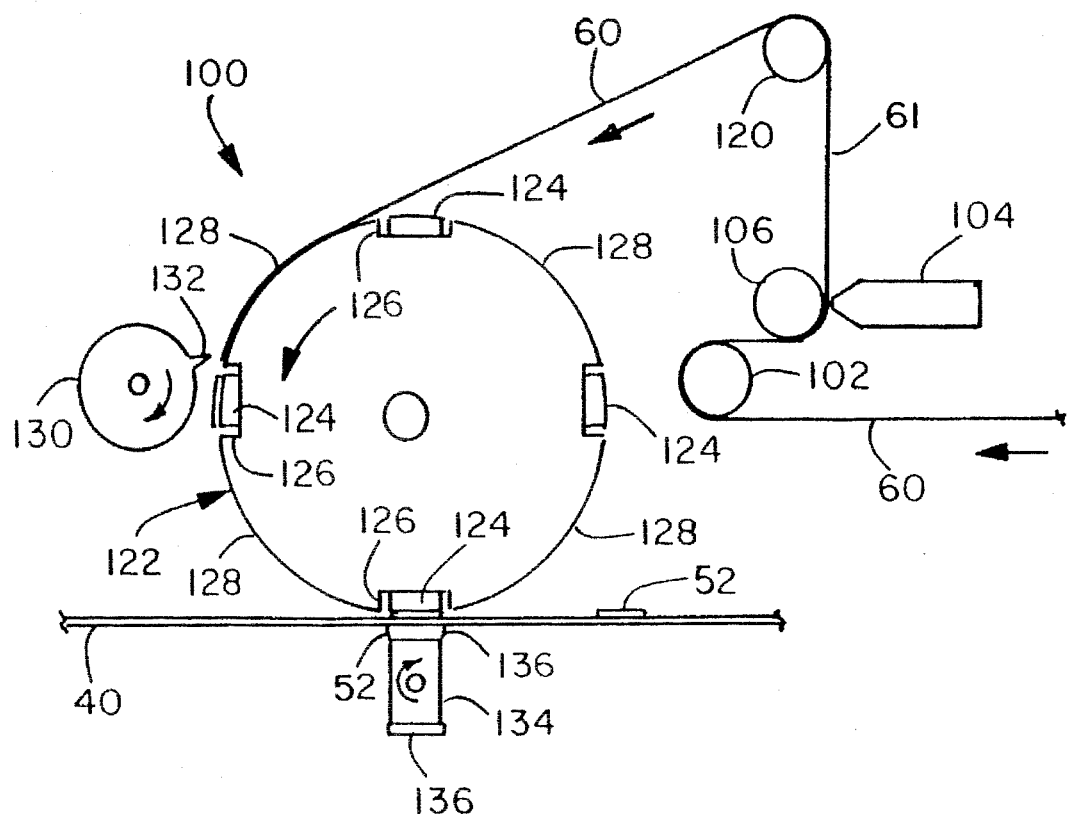
Figure 7:
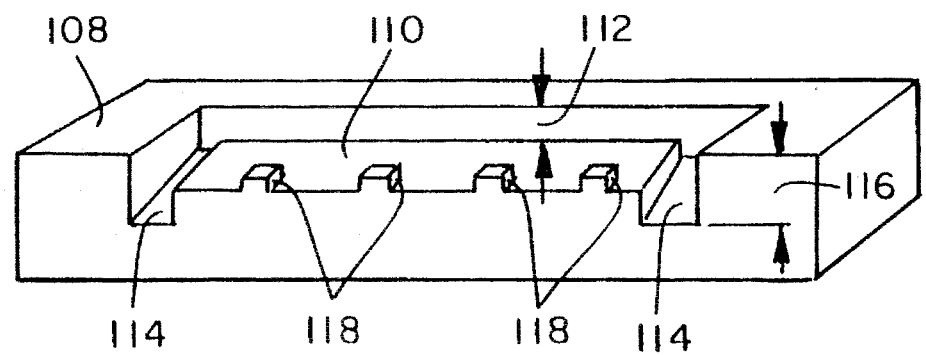

An apparatus 100 for bonding the loop fasteners 52 to the moisture barrier 40 is representatively illustrated in FIGS. 6 and 7. A continuous web of loop material 60 is routed to the apparatus 100 and cut into discrete loop fasteners 52 which are then adhesively bonded to a continuous web of substrate material 40 at spaced locations. The apparatus 100 can also process multiple webs of loop material simultaneously (not shown), and similar equipment may be used to apply the other loop fasteners 52 to the undergarment 20.

The continuous web of loop material 60 is supplied from a supply roll or other source (not shown) and routed in the direction of the arrows shown in FIG. 6. The web of loop material 60 passes over a guide roll 102 and between an adhesive die head 104 and a support roll 106. The die head 104 is operated to apply the adhesive substance 80 (not shown in FIGS. 6 and 7) onto the first major surface 61 of the web of loop material 60. In one particular embodiment, the temperature range of the adhesive is 315° to 325° F. (157.2° to 162.8° C.) and the dwell time of the adhesive is 7.75 to 7.89 seconds.

The die head 104 includes a slotted shim 108 which is separately shown in FIG. 7. The shim 108 includes a central, primary application region 110 having a depth dimension representatively shown by reference numeral 112. The shim 108 also includes a pair of supplemental application regions 114 which flank the primary application region 110. The supplemental application regions 114 each have a depth dimension representatively shown by reference numeral 116. Operation of the die head 104 causes the adhesive substance 80 to flow over the primary and supplemental application regions 110 and 114 of the shim 108 and onto the web of loop material 60. The differing depth dimensions of the primary and supplemental application regions 110 and 114 function to form the first zone 81 and the second zones 82 having different basis weights. The width of the supplemental application regions 114 is desirably large enough for the adhesive to be able to readily enter the supplemental application regions to the full depth dimension.

In particular embodiments, the supplemental application regions 114 may have a depth dimension 116 that is at least about twice as great as the depth dimension 112 of the primary application region 110. For purposes of illustration, the depth 112 of the primary application region 110 may be about 0.25 mm (0.01 inch) and the depth 116 of the supplemental application regions 114 may be about 5 mm (0.02 inch). The distance between the supplemental application regions 114 is desirably controlled so that the second zones 82 are positioned in the peripheral portions 76 of the loop fasteners 52. With further reference to FIG. 7, the shim 108 may optionally include a plurality of spaced-apart nubs 118 which function to maintain adhesive flow through the primary application region 110 of the shim 108.

The web of loop material 60 is thereafter routed over a guide roll 120 and to a revolving roll 122. The revolving roll 122 is similar to that disclosed in U.S. Pat. No. 4,608,115 issued Aug. 26, 1986, to Schroth et al., which is incorporated herein by reference. The revolving roll 122 is rotatably mounted on a frame (not shown) and rotates in the direction of the arrow shown in FIG. 6. The revolving roll 122 includes a plurality of rotatable platens 124 for receiving the web of loop material 60, carrying discrete loop fasteners 52, and transferring the loop fasteners to the substrate material 40. The platens 124 are rotatable about axes that are desirably perpendicular to the axis of the revolving roll 122. Each platen 124 is directly mounted on a vacuum plate 126. The platens 124 can slidably rotate on the surface of the vacuum plates 126 while applying vacuum pressure to the loop material 60.

The revolving roll 122 also includes a plurality of slip plates 128 positioned at equal distances about the circumference of the revolving roll. One slip plate 128 is located between each adjacent pair of vacuum plates 126. As the web of loop material 60 engages the revolving roll 122, the web slides over a slip plate 128 and onto a platen 124.

A cutting roll 130 is rotatably mounted adjacent the revolving roll 122. The cutting roll 130 includes a cutting blade 132 that is rotated in the direction of the arrow shown in FIG. 6 to engage the web of loop material 60 on the platens 124. Discrete loop fasteners 52 are thus severed on the platens 124 from the web of loop material 60. The platens 124 then carry the loop fasteners 52 from the cutting roll 130 to the substrate 40 at the location of an applicator roll 134. The cut loop fasteners 52 are maintained on the platens 124 from the cutting roll 130 to the applicator roll 134 by operation of the vacuum plates 126. The platens 124 can be rotated at this stage to change the angle at which the loop fasteners 52 are applied to the substrate 40.

The applicator roll 134 is rotatably mounted adjacent the revolving roll 122 so as to rotate in the direction of the arrow shown in FIG. 6. The applicator roll 134 includes striking members 136 comprising resilient material such as rubber. The striking members 136 are alternately rotated into engagement with the substrate 40 to press the substrate against the platens 124. Because the loop fasteners 52 have the adhesive substance 80 applied on their sides facing outward of the revolving roll 122 and toward the substrate 40, the compression of the substrate against the platen 124 will cause the loop fasteners to transfer from the platens and adhere to the substrate.

The strap members 50 (FIG. 1) are each generally rectangular strips of material having opposite forward and rearward end portions 85 and 86. The strap members 50 are preferably formed of an elastic material, which is capable of stretching to approximately 2.8 to 3 times its relaxed length. The strap members 50 preferably have a length from about 6 inches to about 16 inches (ca. 15–41 cm.), and a width from about 0.5 inch to about 2 inches (ca. 1–5 cm.). For example, each strap member 50 may be 11 inches (ca. 28 cm.) long and 1 inch (ca. 2.5 cm.) wide. The cut ends of the strap members 50 may be bonded by ultrasonics, adhesives or other suitable means to prevent raveling.

The hook fasteners 54 are attached at each end portion 85 and 86 of each strap member 50, on the same side of the strap member. The hook fasteners 54 desirably comprise a single-sided hook material and form the hook component of the hook-and-loop attachment system. The hook fasteners 54 may be of a variety of shapes, such as rectangular and measuring about 0.875 inch by about 1.125 inches (ca. 2.2 by 2.9 cm.). Each hook fastener 54 is attached to a strap member 50 by ultrasonic bonds, adhesives, stitches or other suitable means. As illustrated in FIG. 1, each hook fastener 54 may include a free end 88 that is rounded and void of hooks. The free end 88 provides a convenient surface for grasping the hook fastener 54 to remove it from engagement with the loop material 60. The hook fasteners 54 may be positioned in full face-to-face contact with the strap members 50 (not shown), or positioned such that hook fasteners extend past the ends of the strap members (FIG. 1).

Suitable hook material may be molded or extruded of nylon, polypropylene or another suitable material. Desirable stiffness levels of the hook material may be obtained from polymeric materials having a flexural modulus of about 70,000–120,000 pounds per square inch (ca. $4.83 \times 10^8$ –$8.27 \times 10^8$ nt/m$^2$) and a Shore hardness value within the range of about D-40 to D-80, such as D-61. The hook fasteners 54 desirably contain uni-directional hooks, with the machine direction of the hooks aligned with longitudinal axis of the strap member 50, and the hooks directed toward the opposite end portion 85 or 86 of the strap member. One suitable single-sided hook material for the hook fasteners 54 is available from Velcro Industries B.V., Amsterdam, Netherlands or affiliates thereof, and is identified as HTH-840 with No. 22 uni-directional hook pattern.

The shape, density and polymer composition of the hooks may be selected to obtain the desired peel and shear force resistance values, as hereinafter described, between the hook fasteners 54 and the loop fasteners 52. One skilled in the art would recognize, for instance, that a mere aggressive hook material may comprise a material with a greater average hook height, a greater percentage of directionally-aligned hooks, or a more aggressive hook shape. As one example, the density of the hook members may be more than 50 hooks per square inch (ca. 8 per square cm.), and mere particularly within the range of about 440 to about 1040 hooks per square inch (ca. 68–161 per square cm.), such as about 740 hooks per square inch (ca. 115 per square cm.). The row density may be within the range of about 20 to about 60 rows per linear inch of width (ca. 8–24 per linear cm.), such as about 40 rows per linear inch of width (ca. 16 per linear cm.). The hook members may be hook-shaped, mushroom-shaped, arrow-shaped or any other desired shape.

In use, the undergarment 20 is positioned on the body of the wearer and secured in position using the attachment system. The wearer can engage one hook fastener 54 of each strap member 50 with one of the loop fasteners 52 in the back waist region 32. After stretching or relaxing the strap members 50 to obtain the desired tension therein, the wearer can then engage the opposite hook fasteners 54 of each strap member 50 with one of the corresponding loop fasteners 52 in the front waist region 30. The angled orientation of the loop fasteners 52 prompts the wearer to secure the hook fasteners 54 so that the strap members 50 are aligned with the longitudinal axis of the front loop fasteners 52, beneficially causing the strap members to be positioned toward the hips of the wearer.

The adhesive substance 80 functions to securely bond the loop material 60 to the moisture barrier substrate 40. The loop fastener 52 thereby resists delamination in response to shear forces generated by engagement with the hook fastener 54. The increased basis weight of the second zone 82 is largely but not entirely responsible for the secure bond of the loop material 60 to the substrate 40. Furthermore, the relatively small area of the second zone 82 and its application to the peripheral portions 76 means that relatively few loops 66 will be deadened as a result of bleed through of adhesive 80 from the second zone. The medial region 74 will be bonded to the substrate as well although the loops 66 in the medial region will remain available for engagement with the hook fasteners 54.

Figure 8:
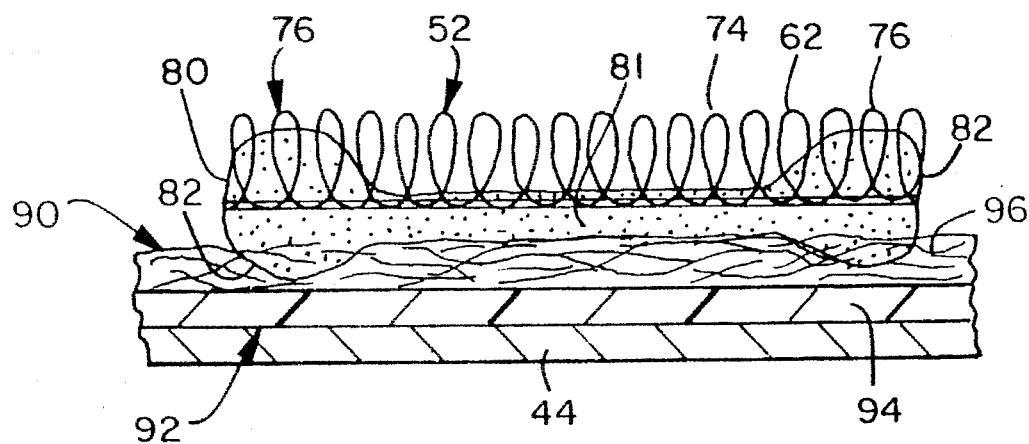

An alternative undergarment 90 according to the present invention is illustrated in FIG. 8, where components similar to those previously described have the same reference numeral. The undergarment 90 includes a moisture barrier 92 comprising an inner liquid impermeable layer 94 and an outer fibrous layer 96. In one particular embodiment, the inner layer 94 comprises a cast or blown film formed of polypropylene, polyethylene or the like, and the outer layer 96 comprises a spunbond web formed of polypropylene and polyethylene medium-crimped bicomponent fibers in a 50/50 side-by-side configuration. The inner and outer layers 94 and 96 may be bonded together such as by a patterned application of adhesive, by thermal bonds, or other suitable means. The adhesive substance 80 is bonded directly to the outer layer 96. As suggested by FIG. 8, the second zones 82 of the adhesive substance 80 tend to more thoroughly penetrate the fibers of the outer layer 96 to better secure the peripheral portions 76 of the loop fastener 52 to the moisture barrier 92.

In general, the adhesive substance 80 having first and second zones 81 and 82 with the above-reference properties may be used with a variety of disposable absorbent products. Examples of diaper configurations, for instance, are disclosed in U.S. patent application Ser. No. 08/168,615 by T. Roessler et al., filed Dec. 16, 1993, and titled "Dynamic Fitting Diaper" (Attorney Docket No. 10,961); and U.S. patent application Ser. No. 08/168,615 by E. D. Johnson et al., filed Aug. 12, 1994, and titled "Diaper With Improved Lateral Elongation Characteristics" (Attorney Docket No. 11,629). The adhesive substance 80 having first and second zones 81 and 82 with the above-reference properties may, in fact, be used bond any type of flexible fabric such as a mechanical fastener to a substrate.

The following EXAMPLES are provided to give a more detailed understanding of the invention. The particular amounts, proportions, compositions and parameters are meant to be exemplary, and are not intended to specifically limit the scope of the invention.

TEST EXAMPLE 1

A number of test undergarments having the general configuration of the undergarment 20 shown in FIG. 1 were constructed. In each test undergarment, one of the loop fasteners 52 from the back waist region 32 was bonded to the moisture barrier using an adhesive substance 80 having designated first and second zones 81 and 82. The remaining three loop fasteners 52 of the test undergarments were bonded to the moisture barrier with the same adhesive substance 80 applied at a generally constant basis weight.

The test undergarment included a moisture barrier 92 as described in relation to FIG. 8 which comprised an adhesive laminate of an inner layer 94 and an outer layer 96. The inner layer 94 was formed of a polyethylene film having a basis weight of about 24 grams per square meter and a thickness of about 0.025 millimeter. The outer layer 96 comprised a point bonded spunbond nonwoven formed of polypropylene and polyethylene medium-crimped bicomponent fibers in a 50/50 side-by-side configuration. The outer layer 96 had a basis weight of about 42.25 grams per square meter.

The test undergarment also included an absorbent assembly 42 disposed on the moisture barrier 92 and a bodyside liner 44 disposed on the absorbent assembly. The bodyside liner 44 comprised a spunbond polypropylene web. The absorbent assembly 42 was formed of cellulose fluff, sprayed polypropylene filaments, and superabsorbent particles. The absorbent assembly 42 was wrapped in tissue and attached to the moisture barrier 92 using a construction adhesive. The bodyside liner 44 was positioned over the absorbent assembly 42 and bonded to the outer periphery of the moisture barrier 92. The test undergarment also include elastic leg members 46 secured along the two side margins 38 in the crotch region 34 of the garment.

The fastening system for the test undergarment included the four loop fasteners, which were formed of a tricot warp knit, brushed (napped) polyester yarn fabric purchased from Guilford Mills (No. 33517). A vinyl acetate copolymer sizing (RESYN 5904 from National Starch and Chemical Corp.) had been mist deposited on the back face of the loop material prior to heat treatment to obtain a final concentration of less than 4 weight percent. The two loop fasteners 52 in the front waist region 30 measured 1.25×3.37 inches and were positioned to form an angle of about 33 degrees with the transverse axis. The two loop fasteners 52 in the back waist region 32 measured 1.5×2.0 inches and were aligned with the transverse axis 24 of the garment.

The adhesive substance 80 used to attach the loop fasteners 52 to the moisture barrier substrate 92 comprised a styrene-isoprene-styrene block copolymer based adhesive with a rosin ester tackifying resin from Findley Adhesives, Inc. One of the loop fasteners 52 in the back waist region 32 was bonded to the moisture barrier 92 using a multiple level slotted shim as shown in FIG. 7. The other three loop fasteners 52 were bonded to the moisture barrier 92 using a single level shim so that the adhesive substance 80 was applied at a generally constant basis Weight.

The two elastic strap members 50 were formed of an elastic material purchased from Shelby Elastics of Shelby, N.C., U.S.A. The strap members 50 had a length of about 10.5 inches (26 cm.) and a width of about 1 inch (2.5 cm.). The strap ends were ultrasonically bonded to prevent raveling. The hook fasteners 54 that were bonded to each end of each strap member 50 were purchased from Velcro USA and identified as No. HTH-840 including 22 Series hooks.

The hook fasteners 54 measured 0.876×1.625 inches (2.23× 4.13 cm) and had the unidirectional hooks pointing toward the center of the strap. Each hook fastener 54 had three rows of hooks at a free end ultrasonically deformed to form finger tabs. The hook fasteners 54 were ultrasonically bonded to the strap members 50.

Comparative Example 1

For purposes of comparison, comparative undergarments were also constructed. All of the loop fasteners 52 in the comparative undergarments were bonded to the moisture barrier substrate 92 using a single level shim so that the adhesive substance 80 was applied at a generally constant basis weight. In all other respects, the comparative undergarments were the same as the test undergarments.

The test and comparative undergarments were both examined to determine the distribution of the adhesive substance 80 in the finished product. The basis weight of the adhesive substance 80 was determined according to the Basis Weight Test as set forth in the TEST PROCEDURES section below. The loop fastener 52 on the test undergarment that had the adhesive 80 applied using the multiple level slotted shim was found to have a first zone 81 measuring 3.0 by 3.8 cm for an area of 11.4 cm$^2$ and two second zones 82 each measuring 3.0 by 0.3 cm for a combined area of 1.8 cm$^2$. On one of the test undergarments, the first zone 81 weighed 0.0538 g for a basis weight of 0.00472 g/cm$^2$, and the second zones 82 had a combined weight of 0.0350 g for an average basis weight of 0.0194 g/cm$^2$. On a second test undergarment, the first zone 81 weighed 0.0532 g for a basis weight of 0.00467 g/cm$^2$, and the second zones 82 had a combined weight of 0.0354 g for an average basis weight of 0.0197 g/cm$^2$. The comparably positioned loop fasteners 52 on the comparative undergarments were found to have a single, generally uniform distribution of adhesive. On one of the comparative undergarments, the adhesive measured 3 by 4.4 cm for an area of 13.2 cm$^2$, and weighed 0.0897 g for a basis weight of 0.0068 g/cm$^2$. On a second comparative undergarment, the adhesive measured 3 by 4.45 cm for an area of 13.35 cm$^2$, and weighed 0.0889 g for a basis weight of 0.0067 g/cm$^2$.

The hook-and-loop fastening systems of both the test undergarments and the comparative undergarments were also evaluated for their resistance to shear forces. The fastening systems were evaluated according to the Hook And Loop Shear Test as set forth in the TEST PROCEDURES section below. A comparison of the shear resistance of the loop fastener 52 of the test undergarment that was attached with the adhesive substance 80 applied in zones 81 and 82 of different basis weight to the comparably positioned loop fastener 52 of the comparative undergarment is set forth in Table 1. Three sets of 20 test undergarments and one set of 20 comparative undergarments were tested.

TABLE 1

| | Hook And Loop Shear Test (reported in pounds) | | | |
|---|---|---|---|---|
| Specimen | Test Undergarment | | | Comparative |
| Number | Set 1 | Set 2 | Set 3 | Undergarment |
| 1 | 11.75 | 11.75 | 14.15 | 10.00 |
| 2 | 11.60 | 12.75 | 13.30 | 8.70 |
| 3 | 13.45 | 12.05 | 12.95 | 9.70 |
| 4 | 12.50 | 12.45 | 12.40 | 10.20 |
| 5 | 13.10 | 12.50 | 14.00 | 10.00 |
| 6 | 12.80 | 12.90 | 14.15 | 9.90 |
| 7 | 13.00 | 13.55 | 14.80 | 9.75 |
| 8 | 12.30 | 13.25 | 12.05 | 10.05 |

TABLE 1-continued

| | Hook And Loop Shear Test (reported in pounds) | | | |
|---|---|---|---|---|
| Specimen | Test Undergarment | | | Comparative |
| Number | Set 1 | Set 2 | Set 3 | Undergarment |
| 9 | 12.90 | 13.70 | 12.85 | 9.85 |
| 10 | 13.15 | 14.10 | 13.00 | 11.05 |
| 11 | 12.50 | 12.50 | 12.85 | 10.50 |
| 12 | 13.65 | 12.55 | 13.45 | 10.65 |
| 13 | 13.15 | 12.80 | 14.65 | 9.80 |
| 14 | 12.25 | 13.50 | 11.25 | 9.50 |
| 15 | 12.80 | 12.60 | 13.85 | 9.80 |
| 16 | 13.35 | 12.60 | 12.30 | 9.45 |
| 17 | 13.55 | 12.50 | 11.70 | 9.70 |
| 18 | 12.95 | 13.50 | 13.75 | 10.05 |
| 19 | 13.45 | 12.60 | 13.60 | 10.10 |
| 20 | 13.45 | 12.35 | 12.40 | 10.40 |
| Average | 12.88 | 12.83 | 13.17 | 9.96 |
| Stnd. Deviation | 0.58 | 0.59 | 0.97 | 0.49 |

The three sets of test undergarments had shear resistance values of 12.88 pounds (5.84 kg), 12.83 pounds (5.82 kg), and 13.17 pounds (5.97), The comparative undergarment had a significantly lower shear resistance value of 9.96 pounds (4.52 kg). For all shear resistance values recorded except one, the loop fastener separated from the substrate material. The exception was the thirteenth specimen of set 3 of the test undergarment, where the hook fastener pulled away from the loop fastener.

TEST PROCEDURES

Basis Weight Test

This test has been designed to measure the basis weight of an adhesive substance which may be used in an absorbent article, such as a disposable absorbent undergarment. A portion of the product to be tested is cut from the product. The portion should measure at least about 6 by 7 cm, with the longer dimension parallel to the transverse axis of the product and the shorter dimension parallel to the longitudinal axis of the product. The portion should include the entire fastener to be tested, and can be made larger if necessary to include the entire fastener.

Place the portion on a smooth, stiff cardboard surface, oriented so that the longer dimension of the portion lies left to right. With a glass microscope slide as a straight edge oriented parallel with the longer direction, trim off the top and bottom sections of the portion to leave a 3.0 cm middle section. Peel off any portions of the product such as the moisture barrier that can be removed without loosing any adhesive. This resulting sample should measure 3 cm by the width of the fastener and consist of the fastener, the adhesive, and some other fibers that could not be peeled from the sample. Note that the sample orientation or the 3 cm dimension may need to be changed if this results in the removal of significant zones of adhesive.

Place the sample on a couple of thick pieces of poly film such as page protectors and place the combination on a light table. Examine the sample for relatively dark areas which represent thicker areas of adhesive. With a fresh razor blade, bear down through the fastener and into the poly film, immediately adjacent to the thicker areas of adhesive. Cut the sample into specimens which appear to have common thicknesses of adhesive. Measure the area of each specimen, including only areas actually covered by adhesive.

Weigh each specimen. Remove adhesive from each specimen by chloroform ($CHCl_3$) extraction at room temperature. Evaporate to dryness and re-weigh each specimen to determine the weight of adhesive that had been part of the specimen. The basis weight of the adhesive for a particular specimen is the adhesive weight divided by the surface area.

Hook And Loop Shear Test

The Hook And Loop Shear Test measures the force needed to shear a loop fastener from the underlying substrate material or the force needed to disengage the hook fastener from the loop fastener, whichever fails first. In general, twenty specimens of loop or other first fasteners are cut from the product such as an undergarment to which they are attached. Then a hook or second fastener is applied to the designated loop fastener, engaged by applying pressure with a roll down, inserted into tensile testing jaws, and pulled until either the hook fastener disengages the loop fastener or the loop fastener delaminates from the substrate material. Pass or fail and the mode of separation are documented. The shear value for a particular configuration of fastener component is the average of the twenty values obtained in the test.

The test employs the following equipment and materials:

1. Marker, permanent (e.g. Stanford Sharpie)
2. Paper cutter, for example a paper cutter identified as Jacques, Jr. from TMI, Amityville, N.Y. 11701.
3. Scissors
4. Roll down, 4.5 lb., hand held, such as one available from Chemsultants International, Mentor, Ohio, 44061-1118.
5. MecMesin End Seal Tester with a Chatilion DF150 Digital Gauge, 3-inch fabric grips and a fixed 12"/min. (300 mm/min) speed. The end seal tester employs a test stand identified as Model M1-000EL 200 lb. capacity with 1.6–31.5 in/min speed option, obtained from Mec-Mesin Inc., Santa Rosa, Calif. U.S.A. The gauge is identified as Model DFIS-50 force gauge with 50 lb. cell, and the fabric grips are identified as Model GF-7 fabric roller grips 3 inch wide. Both the gauge and grips can be obtained from Chatilion and Sons Inc., Greensboro, N.C. U.S.A.
6. Calibration weight(s) used to verify the accuracy of the Chatilion Gauge; traceable to the National Institute of Standards and Technology and within the range of values usually tested.
7. Hook strap comprising a hook fastener bonded to a strap formed of elastic material. The strap is approximately 13 cm long and 2.5 cm wide and can be obtained from Shelby Elastics. The hook fastener is bonded to one end of the strap. The hook fastener measures 2.23 by 4.13 cm and includes uni-directional hook material identified as HTH 840 No. 22 available from Velcro Industries B.V., pointing in the direction of the strap.
8. Ruler, millimeter increments Proper training is essential for the proper execution of this procedure. The technician should also practice before attempting to do the test. In particular, it is important that the tester is properly trained on how to use the roller in order to maintain a constant weight. When using the hand held roll down hold the roller handle lightly at the end with the storage support legs pointing up, and always keep the handle parallel to the material being rolled. Lift up the roller handle slightly so that the pin is just touching the bottom of the pin hole. The weight applied to the hook fastener should come only from the roller, not from the technician or the handle. When the rolldown is not in use, the handle should be flipped over.

Samples products are collected and labeled. To avoid any damage to the hook or loop materials prior to testing, avoid excessive handling of the product/materials. The hook and loop material should not come into contact with each other prior to testing. The specimens to be tested are prepared in the following manner.

1. Lay out the product with the loop fasteners facing up.
2. Using either a scissors or cutting board, cut the loop fastener out of the product, leaving 40 millimeters of the substrate material along the edge of the loop fastener toward the center of the product and 15 millimeters of substrate material, if available, along all other edges of the loop fastener. Remove any fluff from the specimens.
3. Carefully label each loop fastener so that the relative location of the loop fastener on the product is known.
4. Gently lay a hook strap on each of the loop fasteners so that the hook fastener is centered on the loop fastener and the strap is positioned over the 40 mm section of the substrate material. If possible, make sure there is 20 mm of loop material between the hook fastener and the end of the loop fastener that is remote from the 40 mm section of substrate material. Note the hooks must be attached to the loop material.
5. Roll the hooks using the 4.5 lb. roller. Make 3 cycles over each hook. One cycle is defined as one pass over the specimen then a second pass in the opposite direction. When one cycle has been completed the roller will be at the starting point. Count 1 second in each direction.

The equipment is then set up in the following manner. Equipment manufacturers or their literature should be consulted for specific calibration information.

1. Turn on the power to the Chatilion gage by switching the toggle to the "ON" position.
2. Turn on the power to the base of the MecMesin Test Stand. Allow the gage to warm up for a minimum of 15 minutes.
3. On the gage, press the units button until the "lb" measurement appears in the digital display window. If metric units are desired, press UNITS button until "KG" appears in the display window.
4. Adjust the distance between the clamps to 2.5 inches (63.5 mm) by moving the lower limit adjustment collar. Set the upper collar at a distance that allows the specimen to completely separate.

Each specimen is then tested according to the following procedure.

1. Insert the specimen so that it is centered in the jaw width and the hook side of the specimen is facing toward the tester. When closing the upper jaw, make sure the specimen is level and the loop fastener is below the jaw clamp. Only the 40 mm long tab of substrate material that extends beyond the loop fastener should be clamped in the upper jaw.
2. Tuck the tab of substrate material behind the lower clamp and position the strap in the lower jaw so the strap-to-hook fastener bond area is just above the lower jaw. Center the strap. It is important that the hook/loop interface is centered and vertical between the jaws. If it is not straight, open the jaws and reclamp the specimen.
3. Press the ZERO on the Mecmesin control panel The gauge will read "00.00". This display is required for each specimen.
4. Begin the test by moving the control panel UP/DOWN switch to the UP position. If the substrate material slips in the lower jaw, hold the lower jaw down against the specimen.
5. Upon complete separation of either the hook/loop or loop/substrate, return the upper jaw by moving the switch to the "Down" position.
6. Record the peak value that is displayed and the mode of failure.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. A method of forming a fastening component, comprising the steps of:

providing a first fastener comprising a flexible fabric;

providing substrate; and applying an adhesive substance between the first fastener and the substrate and bonding the adhesive substance to both the first fastener and the substrate, the adhesive substance comprising:

a first zone having a first basis weight greater than zero; and a second zone having a second basis weight at least about 1.5 times greater than the first basis weight.

2. The method of claim 1, wherein the step of applying the adhesive substance comprises causing the adhesive substance to flow over a slotted shim having a primary application region and at least one supplemental application region, the supplemental application region having a depth dimension at least twice as great as a depth dimension of the primary application region.

3. The method of claim 1, wherein the second basis weight is at least about 2 times greater than the first basis weight.

4. The method of claim 3, wherein the second basis weight is from about 4 to about 20 times greater than the first basis weight.

5. The method of claim 1, wherein the first zone covers a first area, the second zone covers a second area, and the first area is at least about 6 times greater than the second area.

6. The method of claim 1, wherein the first fastener has a first major surface and a second major surface, and the second major surface comprises a plurality of loops adapted for releasable engagement with a complementary fastener.

7. The method of claim 1, wherein the substrate comprises an inner liquid impermeable layer and an outer fibrous layer, and the adhesive substance is bonded directly to the outer fibrous layer.

8. A method of forming a fastening component, comprising the steps of:

providing a first fastener comprising a flexible fabric, the first fastener having a first major surface, a second major surface, a medial region, and peripheral portions surrounding the medial region;

providing a substrate; and applying an adhesive substance between the first major surface and the substrate and bonding the adhesive substance to both the first major surface and the substrate, the adhesive substance comprising:

a first zone disposed on the medial region and having a first basis weight greater than zero; and an abutting second zone disposed on the peripheral portions and having a second basis weight at least about 1.5 times greater than the first basis weight.

9. The method of claim 8, wherein the step of applying the adhesive substance comprises causing the adhesive substance to flow over a slotted shim having a primary application region and at least one supplemental application region, the supplemental application region having a depth dimension at least twice as great as a depth dimension of the primary application region.

10. The method of claim 8, wherein the second basis weight is at least about 2 times greater than the first basis weight.

11. The method of claim 10, wherein the second basis weight is from about 4 to about 20 times greater than the first basis weight.

12. The method of claim 8, wherein the first zone covers a first area, the second zone covers a second area, and the first area is at least about 6 times greater than the second area.

13. The method of claim 8, wherein the second major surface comprises a plurality of loops.

14. The method of claim 8, wherein the medial region has a surface area of from about 40 to about 98 percent of a surface area of the first fastener.

15. The method of claim 8, wherein the substrate comprises an inner liquid impermeable layer and an outer fibrous layer, and the adhesive substance is bonded directly to the outer fibrous layer.

* * * * *